(12) United States Patent
Egle

(10) Patent No.: US 7,311,717 B2
(45) Date of Patent: Dec. 25, 2007

(54) DEVICE FOR GENERATING AN ARTIFICIAL CONSTRICTION IN THE GASTROINTESTINAL TRACT

(75) Inventor: Walter Egle, Koblach (AT)

(73) Assignee: AMI Agency for Medical Innovations GmbH, Götzis (AT)

( * ) Notice: Subject to any disclaimer, the term of this patent is extended or adjusted under 35 U.S.C. 154(b) by 573 days.

(21) Appl. No.: 10/857,924

(22) Filed: Jun. 2, 2004

(65) Prior Publication Data
US 2004/0267377 A1 Dec. 30, 2004

(30) Foreign Application Priority Data
Jun. 4, 2003 (AT) .............................. A 863/2003

(51) Int. Cl.
*A61B 17/08* (2006.01)
*A61B 17/00* (2006.01)
*A61F 2/04* (2006.01)

(52) U.S. Cl. .................. 606/153; 606/201; 600/37
(58) Field of Classification Search ............... 606/153, 606/201–203; 600/30–32, 37, 207; 604/288.01–288.04
See application file for complete search history.

(56) References Cited
U.S. PATENT DOCUMENTS

| | | | | |
|---|---|---|---|---|
| 2,660,174 A | * | 11/1953 | Saemann | ................ 606/202 |
| 3,713,446 A | * | 1/1973 | Sarnoff | ................ 606/202 |
| 3,730,186 A | * | 5/1973 | Edmunds et al. | ........... 606/202 |
| 4,592,339 A | | 6/1986 | Kuzmak et al. | |
| 4,773,419 A | * | 9/1988 | Tountas | ................ 606/202 |
| 6,067,991 A | * | 5/2000 | Forsell | ................ 600/30 |
| 6,470,892 B1 | | 10/2002 | Forsell | |
| 6,511,490 B2 | | 1/2003 | Robert | |

FOREIGN PATENT DOCUMENTS

| | | |
|---|---|---|
| EP | 0 702 529 | 3/1996 |
| WO | 03/020183 | 3/2003 |

* cited by examiner

*Primary Examiner*—Julian W. Woo
(74) *Attorney, Agent, or Firm*—Wenderoth, Lind & Ponack, L.L.P.

(57) ABSTRACT

A device for generating an artificial constriction in the gastrointestinal tract comprises a band, which can be placed annularly about a particular portion of the gastrointestinal tract, and, by means of a piston-cylinder unit, the size of the passageway opening of the portion of the gastrointestinal tract encompassed by the band is variable, and the band, in the proximity of its first end, is connected with the cylinder of the piston-cylinder unit. The band is connected in the proximity of its second end with the piston of this piston-cylinder unit.

20 Claims, 1 Drawing Sheet

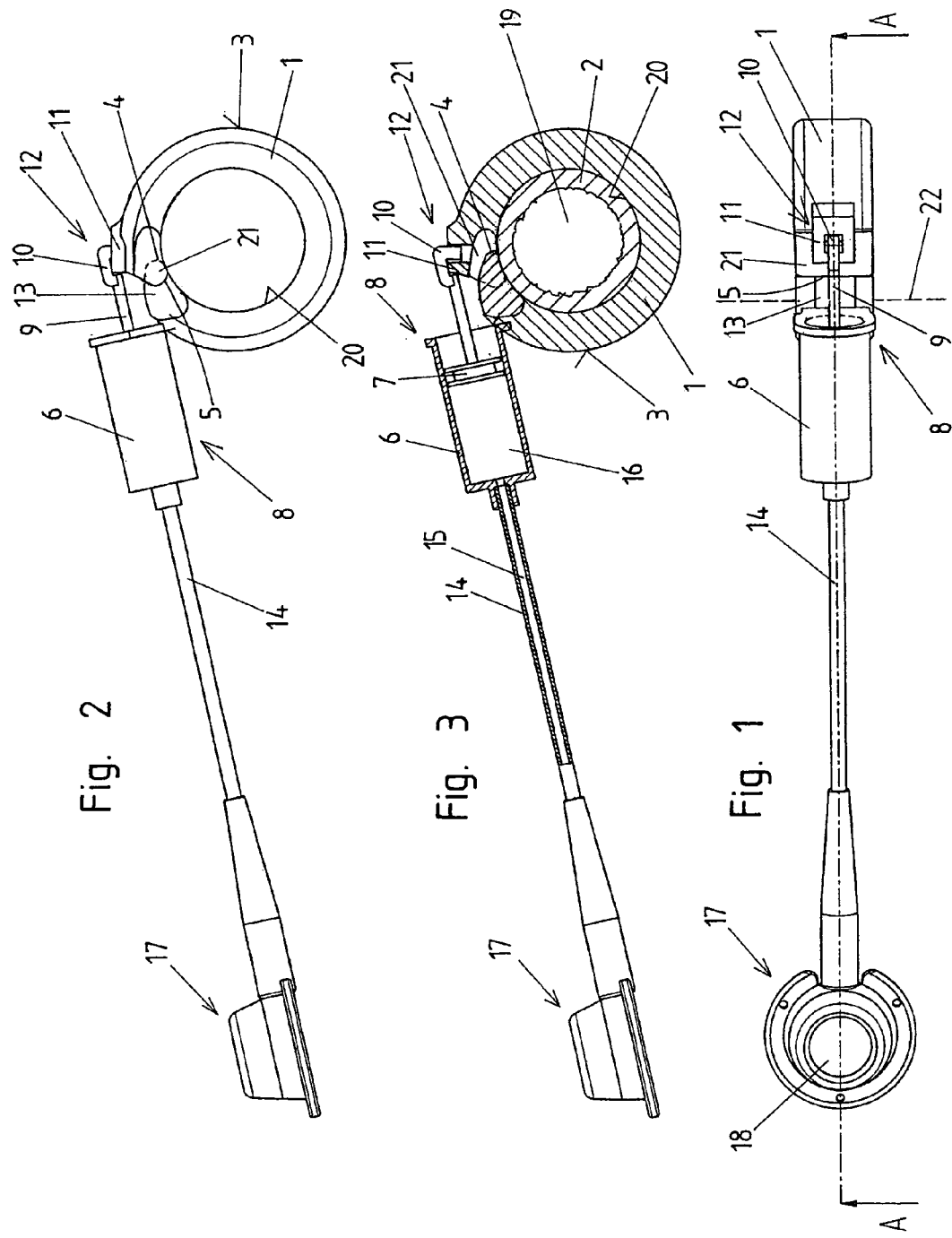

DEVICE FOR GENERATING AN ARTIFICIAL CONSTRICTION IN THE GASTROINTESTINAL TRACT

BACKGROUND OF THE INVENTION a) Field of the Invention

The invention relates to a device for generating an artificial constriction in the gastrointestinal tract with a band, which can be placed annularly about a particular portion of the gastrointestinal tract. By means of a piston-cylinder unit, the size of the throughlet opening of the portion of the gastrointestinal tract, encompassed by the band, can be varied. The band is connected in the proximity of its first end with the cylinder of the piston-cylinder unit.

b) Description of Related Prior Art

A device for generating an artificial constriction in the gastrointestinal tract is known for example in the form of a gastric band from EP 0 702 529 B1. The device comprises a band, which can be placed about the inlet of the stomach and which is developed with an inner hollow chamber extending longitudinally. For the closure of the band placed annularly about the inlet to the stomach, the band comprises a closure device with a first closure part, disposed on one end of the band and having an insertion opening, and a second closure part, disposed at the other end of the band, which can be introduced through the insertion opening and can be latched with respect to it. To constrict the cross section of the passageway of the throughlet opening of the band, and consequently of the inlet to the stomach, the hollow chamber of the band is filled with a filling medium, and the quantity of the filling medium depends on the desired passageway cross section. An injection port connected to the band is provided for filling the band with the filling medium. The injection port is implanted under the skin of the patient.

Apart from its development as a stomach band, a device of this type can especially also be developed as an anal band for the closure of an optionally artificial anus.

One problem encountered in such devices is that, sooner or later in the course of their use, they can leak, such that their function is no longer ensured. Surgical removal and replacement of this band is subsequently required, which is tied to a corresponding strain on the patient. Such leaks occur in practice, particularly in the diaphragm delimiting the band toward the throughlet opening. Such leaks can occur, for example, due to material fatigue in the course of use or due to overfilling of the band. For so-called "early" leaks, which occur up to approximately one year after the placement of the band, injury to the band is most often responsible, which injuries have occurred through a surgical instrument during the operative, in particular laparoscopic, placement of the band.

A device of the type described in the introduction is disclosed in U.S. Pat. No. 6,470,892 B1. The band here comprises a core encompassed by a tube. In one embodiment a piston-cylinder unit is provided, whose cylinder is disposed at one end of the band and whose piston is connected with a traction cord to the core, which terminates at a distance from this end of the band. By displacing the piston, the core within the tube is displaced and the band; closed annularly via a closure, is drawn together. Of disadvantage in this band is inter alia its relatively complicated structure.

SUMMARY OF THE INVENTION

One aim of the invention is to provide an improved device of the type described in the introduction, in which the frequency of surgical interventions following implantation of the device is low. A further aim of the invention is to provide a simple and advantageously implemented device of the type described in the introduction.

According to the invention this is achieved through a device for generating an artificial constriction in the gastrointestinal tract with a band, which can be placed annularly about the particular portion of the gastrointestinal tract, and a piston-cylinder unit to change the size of the throughlet opening of the portion of the gastrointestinal tract encompassed by the band, the band being connected in the proximity of its first end with the cylinder of a piston-cylinder unit and, in the proximity of its second end, with the piston of this piston-cylinder unit.

Consequently, in a device according to the invention, the diameter of the band can be varied by means of the piston-cylinder unit. For this purpose the piston is displaced in the cylinder chamber of the cylinder. For example, this displacement can be accomplished by supplying or removing hydraulic fluid through an injection port. The hydraulic fluid may be sterile water. It is conceivable and possible to use other hydraulic fluids which are preferably well tolerated by the body.

Further advantages and details of the invention will be explained in the following in conjunction with the embodiment example of the invention depicted in the enclosed drawing, based on which further additional aims of the invention are evident.

BRIEF DESCRIPTION OF THE DRAWINGS

In the drawings:

FIG. 1 Is a view of an embodiment example of a device according to the invention;

FIG. 2 Is a side view of the embodiment example of FIG. 1; and

FIG. 3 Is a side view partially in section along line AA of FIG. 1.

DESCRIPTION OF THE PREFERRED EMBODIMENT

An embodiment of a device according to the invention and depicted in the figures, is developed as a gastric band and comprises a band 1 to be placed annularly about the corresponding portion 2, shown schematically in FIG. 2, of the gastrointestinal tract, here the stomach, the inlet to the stomach or the esophagus. The band 1, or at least its major portion, is comprised of a foamed material, preferably a foamed silicone material. In the region of its outer surface 3, facing away from the portion 2 of the gastrointestinal tract, the band 1 can be provided with a reinforced backing, for example of solid silicone, connected with the foamed material body. This reinforced backing can extend over the length of the band 1 or at least a large portion of this length (not shown in the figures).

The band 1 has a first end 4 and a second end 5. In the proximity of the first end 4 of band 1, the cylinder 6 of a piston-cylinder unit 8 is disposed on this band 1. In the embodiment depicted, the cylinder 6 is nondetachably connected with the band 1 in the proximity of the outer surface 3 of the band 1. For example, it is adhered on or the material of band 1 is partially injected around it during its production.

In the state of the band 1 in which it is placed about the portion 2 of the gastrointestinal tract, moreover, a connection is formed between band 1 in the proximity of its second end 5 and the piston 7 of the piston-cylinder unit 8. For this purpose, in the depicted embodiment, a piston rod 9 is attached on piston 7. At the free end of piston rod 9 a first closure member 10 is disposed, which, in the drawing, is depicted schematically as a hook-like element. This first closure member 10 cooperates with a second closure member 11 secured in the proximity of the second end 5 of band 1, which second closure element is depicted in the figure schematically as a plate-shaped part with an insertion opening for the hook-like first closure member 10. The closure members 10, 11 together form a closure device 12, by means of which the band in the proximity of its second end 5 can be attached on the piston rod 9. Instead of the formation of this closure device 12 depicted in the figures, different other formations are conceivable and possible, for example snap closures can be developed to be detachable again after they have been closed or nondetachable after their closing.

When this application describes that the connection of the band with the cylinder 6 or the piston 7 takes place in the "proximity of the first or second end", it is intended to indicate that the corresponding connection sites with the band are located either directly on the corresponding end of the band or are spaced apart from the particular end 4, 5 of the band by less than one fourth of the longitudinal extent of the band 1. At least one of these connection sites is preferably spaced apart from the corresponding end 4, 5 of this band 1, such that a projecting segment 13, 21 results. In the depicted embodiment such projecting segments 13, 21 are disposed at both ends 4, 5, and are formed, for example, by end pieces of nonfoamed (solid) silicone connected, for example, adhered, to the foamed material body forming the remaining length of the band 1. When the two closure members 10, 11 of the closure device 12 are connected with one another, segments of band 1 adjoining the two ends 4, 5 overlap when viewed in the circumferential direction, such that band 1 forms a closed ring viewed in side view. Depending on the position of piston 7 in cylinder 6, this overlap increases or decreases, whereby the diameter of the ring increases or decreases.

For forming this overlap, in the depicted embodiment a recess is developed in band 1 starting from the second end 5 or projecting segments 21 of band 1. The projecting segment 13, which forms the first end 4, is of lesser width than the width of this recess and, depending on the position of piston 7, projects to a greater or lesser extent into this recess.

Various other developments of such an overlap of the two end regions of the band, viewed in the circumferential direction, are conceivable and possible. For example, the band 1 in the region of its two ends 4, 5 could comprise segments, whose width is decreased to approximately one half the value of the remaining band, these segments being offset with respect to one another when viewed in the direction of axis 22 of the throughlet opening, and disposed one next to the other in the overlapping region. It would also be conceivable and possible, that a projecting segment at one end of the band overlaps the other end of the band radially within it, and consequently is in contact on a segment, adjoining this other end of the band, on the inner surface 20 of the band 1. This projecting segment in contact on the inner surface 20 of the other end segment of the band could be developed approximately in the form of a wedge forming only a small step on the inner circumference of the band.

The piston-cylinder unit 8 is connected to an injection port 17 via a tubule 14, whose inner channel 15 communicates with the cylinder chamber 16 of the piston-cylinder unit 8. Consequently, the device includes an inner volume, which is formed by cylinder chamber 16, channel 15 and the inner chamber of injection port 17 and is filled with hydraulic fluid, for example sterile water. To change the position of the piston 7 within the cylinder chamber 16, the quantity of hydraulic fluid present in this closed inner volume is changed. For this purpose, the injection port 17 comprises a diaphragm 18 which can be pierced by the needle of a syringe. By means of the needle inserted through the skin of the patient into the diaphragm of the implanted injection port, the hydraulic fluid can be injected into the inner volume of the injection port or be withdrawn from it. After the needle of the syringe has been withdrawn, the relatively thick diaphragm 18 closes tightly again. Such injection ports are known.

For placing the band 1 about portion 2 of the gastrointestinal tract, for example in a laparoscopic procedure, the second closure member 11 disposed in the proximity of the end 5 of band 1, is initially not connected with the first closure member 10. Using a surgical instrument, the band is pulled by its second end 5 about portion 2 of the gastrointestinal tract and the second closure member is subsequently connected with the first closure member 10 disposed on the piston rod 9. The band 1 now annularly encompasses portion 2 of the gastrointestinal tract, as is shown schematically in FIG. 3. To decrease the size of the passageway opening 19 of portion 2 of the gastrointestinal tract to the desired value, the band 1, starting from the condition depicted in the figures, is correspondingly drawn together by means of the piston-cylinder unit 8, whereby the end segments of the band increasingly overlap and the diameter of the band is decreased.

Instead of introducing or withdrawing hydraulic fluid into or from the closed inner volume of the device by means of an injection port, which, in this sense, forms an hydraulic actuation unit for the piston-cylinder unit 8, it would also be conceivable and possible to connect the tubule 14 with its end, facing away from the piston-cylinder unit 8, with an hydraulic actuation unit, which has a variable inner volume. If the device is developed as an openable and closable closure, for example as an anal band, the hydraulic actuation unit would need to be switchable in known manner between two sizes of its inner volume corresponding to the closed and opened condition of the device.

Different modifications of the depicted embodiment example of the invention are conceivable and possible without going beyond the scope of the invention. For example, the piston rod 9 could also be nondetachably connected, for example adhered on or injected, with the band 1 in the region of its second end 5, and the cylinder 6 could be connectable with band 1 via a first closure part, disposed on cylinder 6, and a second closure part, disposed on band 1 in the proximity of its first end 4.

After both closure members 10, 11 have been connected with one another, the device is advantageously developed such that the inner circumference, facing portion 2 of the gastrointestinal tract, of band 1 is substantially stepless or has only minimal steps, the material of band 1 being relatively soft in the proximity of optionally provided steps (in particular in the region of overlap of the two end segments).

LEGEND OF REFERENCE NUMBERS

1 Band
2 Portion of the gastrointestinal tract
3 External surface
4 First end
5 Second end
6 Cylinder
7 Piston
8 Piston-cylinder unit
9 Piston rod
10 First closure member
11 Second closure member
12 Closure device
13 Projecting segment
14 Tubule
15 Channel
16 Cylinder chamber
17 Injection port
18 Diaphragm
19 Passageway opening
20 Inner surface
21 Projecting segment
22 Axis

The invention claimed is:

1. A device for generating an artificial constriction in the gastrointestinal tract, comprising:
a band having a first end and a second end, said band being configured to be annularly placed about the gastrointestinal tract to thereby encompass a portion of the gastrointestinal tract;
a piston-cylinder unit for varying the size of a passageway opening of the portion of the gastrointestinal tract encompassed by said band, said piston-cylinder unit including a cylinder in proximity to said first end of said band and a piston in proximity to said second end of said band;
said band and said piston-cylinder unit being interconnected and arranged such that, in an open state of said device, at least one of said piston and said cylinder is disconnected from one of said first end and said second end of said band to allow said band to be annularly placed about the gastrointestinal tract, and such that, in a closed state of said device, said cylinder is connected to said band at a location in proximity to said first end of said band and said piston is connected to said band at a location in proximity to said second end of said band to form a ring around the portion of the gastrointestinal tract.

2. The device as claimed in claim 1, further comprising a hydraulic actuation unit connected to said piston-cylinder unit, said hydraulic actuation unit being operable to vary a position of said position relative to said cylinder.

3. The device as claimed in claim 2, wherein said hydraulic actuation unit comprises an injection port connected via a tubule with a cylinder chamber of said piston-cylinder unit.

4. The device as claimed in claim 1, wherein said piston-cylinder unit further includes a piston rod on said piston, said piston being connected to said band via said piston rod.

5. The device as claimed in claim 1, further comprising a closure defining a first closure member and a second closure member for connecting said piston-cylinder unit to said band, said closure being operable to change said band from said open state to said closed state after said band has been placed with said closure open about the portion of the gastrointestinal tract.

6. The device as claimed in claim 5, wherein said piston-cylinder unit includes a piston rod on said piston, said first closure member being on one of said piston and said piston rod, and said first closure member being operable to be connected with said second closure member, said second closure being located on said band in the proximity of said second end of said band.

7. The device as claimed in claim 6, wherein said cylinder of said piston-cylinder unit is permanently fixed to said band in the proximity of said first end.

8. The device as claimed in claim 6, wherein a first segment of said band adjoining said first end of said band overlaps a second segment of said band adjoining said second end of said band when said first closure member is connected to said second closure member and said piston rod is parallel to the overlap of the first segment and the second segment of the band.

9. The device as claimed in claim 5, wherein for the connection of said band in the proximity of said first end with said cylinder, a first closure member is disposed on said cylinder, which is connectable with a second closure member disposed on said band in the proximity of said first end of said band.

10. The device as claimed in claim 9, wherein said piston is permanently fixed to said band in the proximity of said second end.

11. The device as claimed in claim 5, wherein a first segment of said band adjoining said first end of said band overlaps a second segment of said band adjoining said second end of said band when said first closure member is connected to said second closure member.

12. The device as claimed in claim 11, wherein at one of said first end and said second end of said band, a recess is developed which extends from said one of said first segment and said second segment of said band in the circumferential direction of said band and into which projects the other one of said first segment and said second segment of said band.

13. The device as claimed in claim 1, wherein said band is comprised at least substantially of silicone.

14. The device as claimed in claim 1, wherein at least in the proximity of one of said first end and said second end of said band, a projecting segment is provided extending in a direction toward the other one of said first end and said second end of said band starting at one of the connection of said cylinder to said band and said connection of said piston to the band.

15. The device as claimed in claim 1, wherein said piston of said piston-cylinder unit comprises a single piston slidably arranged in said cylinder.

16. The device as claimed in claim 15, wherein said first end of said band is directly connected to said cylinder, and said single piston is operable to be connected to said second end of said band.

17. The device as claimed in claim 16, wherein said band includes a one piece body portion for contacting the gastrointestinal tract, said one piece body portion being continuous and integral between said first end and said second end of said band.

18. The device as claimed in claim 1, wherein said band is directly connected to said cylinder, and said single piston is operable to be connected to said second end of said band.

19. The device as claimed in claim 1, wherein said band includes a one piece body portion for contacting the gastrointestinal tract, said one piece body portion being continuous and integral between said first end and said second end of said band.

20. The device as claimed in claim 1, wherein said piston-cylinder unit is disposed outside said ring formed by said band.

* * * * *